United States Patent
Samuel et al.

(10) Patent No.: US 9,719,108 B2
(45) Date of Patent: *Aug. 1, 2017

(54) NANOPARTICLE MEDIATED DELIVERY OF SEQUENCE SPECIFIC NUCLEASES

(71) Applicant: Dow AgroSciences LLC, Indianapolis, IN (US)

(72) Inventors: Jayakumar Pon Samuel, Carmel, IN (US); Joseph F. Petolino, Zionsville, IN (US); Narasimha Chary Samboju, Carmel, IN (US); Steven R. Webb, Westfield, IN (US); Kerrm Y. Yau, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,864

(22) Filed: Sep. 22, 2015

(65) Prior Publication Data

US 2017/0022521 A1 Jan. 26, 2017

Related U.S. Application Data

(63) Continuation of application No. 12/755,447, filed on Apr. 7, 2010, now Pat. No. 9,187,755, and a continuation-in-part of application No. 12/245,685, filed on Oct. 3, 2008, now Pat. No. 8,722,410.

(60) Provisional application No. 61/167,389, filed on Apr. 7, 2009, provisional application No. 60/978,059, filed on Oct. 5, 2007.

(51) Int. Cl.
| | |
|---|---|
| *C12N 15/90* | (2006.01) |
| *C12N 15/82* | (2006.01) |
| *C12N 5/04* | (2006.01) |
| *C12N 9/22* | (2006.01) |
| *C12N 9/96* | (2006.01) |

(52) U.S. Cl.
CPC ............. *C12N 15/902* (2013.01); *C12N 5/04* (2013.01); *C12N 9/22* (2013.01); *C12N 9/96* (2013.01); *C12N 15/8206* (2013.01); *C12Y 301/21004* (2013.01)

(58) Field of Classification Search
None
See application file for complete search history.

(56) References Cited

U.S. PATENT DOCUMENTS

| | | |
|---|---|---|
| 2007/0016985 A1 | 1/2007 | Miller et al. |
| 2009/0104700 A1 | 4/2009 | Samuel et al. |

FOREIGN PATENT DOCUMENTS

| | | |
|---|---|---|
| CN | 1687427 | 10/2005 |
| JP | 2006506082 | 2/2006 |
| JP | 2007521332 | 8/2007 |
| JP | 2008545621 | 12/2008 |
| JP | 5507459 | 5/2014 |
| WO | 2005005643 | 1/2005 |
| WO | 2005081721 | 9/2005 |
| WO | 2007029980 | 3/2007 |
| WO | 2007050715 | 3/2007 |
| WO | 2008021207 | 2/2008 |
| WO | 2009046384 | 4/2009 |

OTHER PUBLICATIONS

Bibikova, Marina et al., "Targeted chromosomal cleavage and mutagenesis in *Drosophila* using zing-finger nucleases," Genetics, Jul. 2002, 1169-1175, vol. 161.
Durai, Sundar et al., "Zinc finger nucleases: custom-designed molecular scissors for genome engineering of plant and mammalian cells," Nucleic Acids research, 2005, pp. 5978-5990, vol. 33, No. 18.
Gonzalez-Melendi P et al., "Nanoparticles as smart treatment delivery system in plants: Assessment of different techniques of microscopy for their visualization in plant tissues." Annals of Botany, Jan. 1, 2008, pp. 187-195, vol. 101, No. 1.
Kajiyama, S. et al., "Novel plant transformation system by gene-coated gold particle introduction into specific cell using ArF excimer laser," Plant Biotechnology, 2007, pp. 315-320, vol. 24.
Moeller Lorena et al., "Engineering with precision: Tools for the new generation of transgenic crops," Bioscience, May 2008, pp. 391-401, vol. 58, No. 5.
Navarro et al.; "Activated and non-activated PAMAM dendrimers for gene delivery in vitro and in vivo." Nanomedicine. 2009 5(3):287-97. Epub Jan. 19, 2009.
PCT International Search Report for International Application No. PCT/US2010/030155, mailed Aug. 10, 2010.
PCT Written Opinion for International Application No. PCT/US2010/030155, mailed Aug. 10, 2010.
Torney et al., "Mesoporous silica nanoparticles deliver DNA and chemicals into plants," Nature Nanotechnology, Nature Publishing Group, May 1, 2007, pp. 295-300, vol. 2, London.
Wu, J. et al., "Custom-designed zinc finger nucleases: what is next?" Cell Mol Life Sci, Nov. 2007, pp. 2933-2944, vol. 64, No. 22.
Singh, Rajesh et al., "Nanoparticle-based targeted drug delivery," Experimental and Molecular Pathology, 2009, pp. 215-223, vol. 86.
Pasupathy, Karthikeyan et al., "Direct plant gene delivery with a poly(amidoamine) dendrimer," Biotechnology Journal, 2008, pp. 1078-1082, vol. 3 .1JP OA.

*Primary Examiner* — Brent Page
*Assistant Examiner* — Jared Shapiro
(74) *Attorney, Agent, or Firm* — Eric J. Kraus; Magleby Cataxinos & Greenwood (57) ABSTRACT

Provided are methods for introducing a sequence-specific nuclease into a plant cell comprising a cell wall. Methods are provided for genetically or otherwise modifying plants and for treating or preventing disease in plant cells comprising a cell wall.

19 Claims, 4 Drawing Sheets

Figure 1 and 2: *E. coli expression of histidine-tagged (1) and non-histidine (2) tagged ZFN-IL1FokI*

Figure 3: Inter-Chromosomal Homologous Recombination Stimulated by IL-1 Zinc Finger-FokI Fusion Protein. A. Target vector; B. Recombinant with re-constituted GFP gene.

Figure 4: *Schematic Representation of plasmid pDAB1585*

Figure 5: BY2-E single cell lines showing GNP mediated YFP internalization 2 hrs after incubation of cells Figure 6: Inter-Chromosomal Homologous Recombination Stimulated by Meganuclease I-SceI protein. A. Target vector; B. Recombinant with re-constituted GFP gene.

Figure 7: *Schematic Representation of plasmid pDAB100375*

US 9,719,108 B2

NANOPARTICLE MEDIATED DELIVERY OF SEQUENCE SPECIFIC NUCLEASES

CROSS-REFERENCE TO RELATED APPLICATIONS

This application is a continuation of U.S. patent application Ser. No. 12/755,447, filed Apr. 7, 2010, pending, the disclosure of which is hereby incorporated herein in its entirety by this reference. This Application claims the benefit of U.S. Provisional Application No. 61/167,389, filed on Apr. 7, 2009. This application is also a continuation-in-part of U.S. patent application Ser. No. 12/245,685, filed Oct. 3, 2008, and published in English as U.S. Patent Publication No. 2009/0104700 A1 on Apr. 23, 2009, which application claims the benefit of U.S. Provisional Application No. 60/978,059, filed on Oct. 5, 2007.

BACKGROUND OF THE INVENTION

The unique properties of nanoparticles can be exploited for delivering DNA into cells. Among the nanoparticles investigated (e.g., tungsten, aluminum, nickel, etc.), Gold NanoParticles (GNP) tend to be excellent candidates for delivery of DNA. The low cytotoxicity and ease of functionalization with various ligands of biological significance make gold nanoparticles a preferential choice for transformation. Gold nanoparticles can range in size from 1.2 nm-600 nm. The commonly used synthesis of GNP produces a negatively charged (e.g., citrate coating) surface for particles from 20-400 nm, whereas smaller 1-10 nm range of GNPs are positively charged. Plasmid DNA, which is sufficiently flexible to partially uncoil its bases, can be exposed to gold nanoparticles. In the case of the citrate-functionalized GNP, the plasmid DNA can partially uncoil. The negative charges on the DNA backbone are sufficiently distant so that attractive van der Waals forces between the bases and the gold nanoparticle cause plasmid DNA to be attached and coat the surface of the gold particle. Whereas, in the case of the positively charged GNP, electrostatic and van der Waals forces can contribute to coating or attachment of the DNA.

In addition to metal nanoparticles, semi-conductor nanoparticles (e.g., quantum dots) ("QD") within the size range of 3-5 nm have also been used as carriers to deliver molecules into cells. DNA and proteins can be coated or linked to the QD surface that is multifunctionalized with a ligand (see, e.g., Patolsky et al. (2003) J. Am. Chem. Soc. 125:13918). Carboxylic acid or amine multifunctionalized QDs can be cross-linked to molecules containing a thiol group (see, e.g., Dubertret et al. (2002) Science 298:1759; Akerman et al. (2002) Proc. Natl. Acad. Sci. U.S.A. 99:12617; Mitchell et al. (1999) J. Am. Chem. Soc. 121: 8122), or an N-hydroxysuccinimyl (NHS) ester group, by using standard bioconjugation protocols (see, e.g., Pinaud et al. (2004) J. Am. Chem. Soc. 126:6115; Bruchez et al. (1998) Science 281:2013). An alternative way is to multifunctionalize QDs via conjugation with streptavidin. The streptavidin conjugates with biotinylated proteins, oligos, or antibodies (see, e.g., Dahan et al. (2003) Science 302:442; Pinaud et al. (2004), supra; Wu et al. (2003) Nature Biotechnol. 21:41; Jaiswal et al. (2003) Nature Biotechnol. 21:47; and Mansson et al. (2004) Biochem. Biophys. Res. Commun. 314:529).

Nanoparticles have been used to deliver plasmid DNA to a variety of animal cells. It has been found that when DNA-coated nanoparticles are incubated with cells not having a cell wall, the cells take up the nanoparticles and begin expressing any genes encoded on the DNA. Where nanoparticle delivery to cells normally having a cell wall is desired, the cell wall is stripped before the addition of the particles to protoplasts (see, e.g., Torney et al. (2007) Nature Nanotechnol. 2:295-300). In plant cells, the cell wall acts as a barrier for the delivery of exogenously applied molecules. Many invasive methods, like the gene gun (biolistics), microinjection, electroporation, and *Agrobacterium*, have been employed to achieve gene and small molecule delivery into these walled plant cells. Delivering small molecules and proteins across the cell wall and into the plant cell would be advantageous for the development of enabling technologies for the in vitro and in vivo manipulation of cells, tissues, and organs of intact plants.

Although well established in bacteria, yeast, animal cells, and moss, gene addition (i.e., the introduction of foreign DNA into a predetermined genomic location) remains a significant challenge in higher plants. Site-specific transgene integration occurs at a very low frequency in plant cells as compared to random integration, even when the incoming DNA contains large stretches of sequence homologous to host DNA (Halfter et al. (1992) Mol. Gen. Genet. 231(2): 186-93; Lee et al. (1990) Plant Cell 2(5):415-25; Miao and Lam (1995) Plant J. 7(2):359-65. For example, a highly efficient *Agrobacterium*-based transfection system and herbicide selection resulted in gene targeting frequencies of up to $5\times10^{-4}$ in rice. Attempts to enhance gene targeting efficiencies in plants have included the use of negative selection markers, and the use of plants genetically engineered to exhibit higher targeting frequencies. These efforts notwithstanding, random DNA integration via non-homologous processes continue to be a major impediment to gene targeting in plants. Given the general utility envisioned for targeted gene addition in the modification of crops for agricultural and industrial biotechnology, a solution to this problem is sorely needed.

In this regard, substantial increases in the frequency of gene targeting in a broad range of plant and animal model systems have been observed following the induction of a DNA double-strand break (DSB) at a specific genomic location in host cells, which stimulates a native cellular process, homology-directed DSB repair. Naturally occurring site-specific endonucleases whose recognition sites are rare in the plant genome have been used in this manner to drive transgene integration into a target sequence previously transferred into the plant genome via random integration. These studies highlight the potential of targeted DSB induction to stimulate gene targeting in plant cells, though the challenge of introducing a DSB in a native locus remains.

In animal cells, the solution to targeted genome modulation/manipulation is achieved through a variety of nucleotide sequence-specific binding proteins such as leucine zippers, zinc finger proteins, etc. These proteins are involved with gene regulation as transcription factors and/or can be used to induce DSB at a native genomic location. The DSB can be provided by several different classes of sequence-specific nucleases such as meganucleases, leucine zippers, zinc finger proteins, etc., and, more recently, the development of novel chimeric versions of these proteins. One of the best described nucleotide-specific binding proteins are the Zinc Finger Proteins (ZFP). The C2H2 zinc finger was discovered in the amphibian transcription factor TFIIIA, and has since been found to be the most common DNA recognition motif in all species of metazoa. The X-ray crystal structure of the C2H2 ZFP, Zif268, revealed a strikingly syllabic mode of protein-DNA recognition, with each zinc finger specifying a 3 or 4 bp subsite in the context of a tandem arrangement, and suggested the possibility of using this peptide motif as a scaffold for DNA binding domains with novel specificities. Since then, a large number of ZFPs engineered to bind novel sequences have been successfully used in many different laboratories in the context of artificial transcription factors and other functional chimeric proteins. The C2H2 zinc finger protein domain has been used as a scaffold for sequence-specific DNA binding (Pavelitch and Pabo (1991) Science 252:809-17) and ZFNs produced by fusing zinc finger protein domains with a sequence-independent nuclease domain derived from the Type IIS restriction endonuclease FokI (Kim et al. (1996) Proc. Natl. Acad. Sci. USA 93(3):1156-60). Engineered ZFNs have been used to drive high-efficiency targeting to an endogenous genomic locus in transformed (Moehle et al. (2007) Proc. Natl. Acad. Sci. USA 104(9):3055-60) and primary human cells (Lombardo et al. (2007) Nature Biotechnol. 25:1298-306).

Initial attempts at using ZFNs in plants have been promising (Lloyd et al. (2005) Proc. Natl. Acad. Sci. USA 102(6):2232-7; Wright et al. (2005) Plant J. 44(4):693-705; Maeder et al. (2008) Mol. Cell 31(2):294-301). A construct carrying a ZFN gene under the control of an inducible promoter along with its corresponding recognition sequence was stably integrated into *Arabidopsis* and shown to introduce targeted mutations resulting from non-homologous end joining at the recognition site at frequencies averaging 7.9% among induced progeny seedlings (Lloyd et al. (2005), supra). Similarly, among 66 tobacco plants regenerated from protoplasts transformed with a ZFN designed to cleave at the SuRA locus, three displayed single base pair deletions at the target site resulting from non-homologous end joining repair (Maeder et al. (2008), supra). Tobacco cells, containing a pre-integrated, non-functional reporter gene missing 600 bp directly flanking a zinc finger recognition sequence, when co-transformed with constructs containing a corresponding ZFN gene and donor DNA homologous to the pre-integrated sequence comprising the missing 600 bp, showed evidence of homology-directed repair of the reporter gene (Wright et al. (2005), supra). Most recently, a yeast-based assay was used to identify ZFNs capable of cleaving a plant endochitinase gene (Cai et al. (2009) Plant Mol. Biol. 69(6):699-709). *Agrobacterium* delivery of a Ti plasmid harboring both the ZFNs and a donor DNA construct comprising a pat herbicide resistance gene cassette flanked by short stretches of homology to the endochitinase locus yielded up to 10% targeted, homology-directed transgene integration precisely into the ZFN cleavage site. It is important to note that other zinc finger designs based on a C3H1 design have been demonstrated in plants (Shukla et al. (2009) Nature 459: 437-41, Cai et al. (2009), supra).

The present invention relates to methods using nanoparticles to non-invasively deliver sequence-specific nucleases into plant cells having a cell wall.

BRIEF SUMMARY OF THE INVENTION

The following embodiments are described in conjunction with systems, tools and methods that are meant to be exemplary and illustrative, and not limiting in scope.

According to the invention, there are provided methods of introducing a sequence-specific nuclease into a plant cell, the method comprising: providing the plant cell having a cell wall; coating a nanoparticle with at least a sequence-specific nuclease; placing the plant cell having a cell wall and the sequence-specific nuclease coated nanoparticle in contact with each other; and allowing uptake of the sequence-specific nuclease coated nanoparticle into the plant cell comprising a cell wall.

In addition to the exemplary aspects and embodiments described above, further aspects and embodiments will become apparent in view of the following descriptions.

DETAILED DESCRIPTION OF THE INVENTION

In the description and tables that follow, a number of terms are used. In order to provide a clear and consistent understanding of the specification and claims, including the scope to be given such terms, the following definitions are provided:

Backcrossing. Backcrossing may be a process in which a breeder repeatedly crosses hybrid progeny back to one of the parents, for example, a first generation hybrid $F_1$ with one of the parental genotypes of the $F_1$ hybrid.

Embryo. The embryo may be the small plant contained within a mature seed.

Nanoparticle. A microscopic particle with at least one nanoscale dimension, usually less than 100 nm. Nanoparticles suitable for use in the present invention may have a size of 1 nm-0.4 um. A quantum dot may have a median diameter of 1 nm-10 nm, preferably 2 nm-4 nm. Nanoparticles as used in the present application include, but are not limited to, gold nanoparticles, tungsten nanoparticles, gold coated nanoparticles, porous nanoparticles, mesoporous nanoparticles, silica nanoparticles, polymer nanoparticles, gelatin nanoparticles, nanoshells, nanocores, nanospheres, nanorods, magnetic nanoparticles, semiconductor nanoparticles, quantum dots, nanomatrices, dendrimeric nanomatrices and combinations thereof.

Quantum dot. A quantum dot is a semiconductor nanoparticle that confines the motion of conduction band electrons, valence band holes, or excitons (bound pairs of conduction band electrons and valence band holes) in all three spatial directions. The confinement can be due to electrostatic potentials (generated by external electrodes, doping, strain, impurities), the presence of an interface between different semiconductor materials (e.g., in core-shell nanocrystal systems), the presence of the semiconductor surface (e.g., semiconductor nanocrystal), or a combination of these. A quantum dot can have a discrete quantized energy spectrum. The corresponding wave functions are spatially localized within the quantum dot, but extend over many periods of the crystal lattice. A quantum dot contains a small finite number (of the order of 1-100) of conduction band electrons, valence band holes, or excitons (i.e., a finite number of elementary electric charges).

Nano-matrices include, but are not limited to, dendrimers. Dendrimers are spheroid or globular nanoparticles that are engineered to carry molecules encapsulated in their interior void spaces or attached to the surface. The molecules are repeatedly branched molecules; the branching allows for polyvalent interactions between the surfaces and bulk materials. An example of a dendrimer is the spherical cationic polyamidoamine (PAMAM) cascade polymers. These polymers consist of primary amines on the surface and tertiary amines in the interior. This type of dendrimer is partially degraded by heat treatment in solvolytic solvents, thereby resulting in less sterical constraint and greater flexibility. The dendrimer's highly positive charge facilitates electrostatic interactions with DNA, and the flexible structure allows the dendrimer to compact when bound to DNA and swell when released from the DNA. The transfection or transformation efficiency is increased as a result of the positive charge and the flexible structural property of the dendrimer. Dendrimers can be obtained from Qiagen (Qiagen, Germantown, Md.); the dendrimers are marketed to the public as SUPERFECT™ Transfection Reagent (Cat #301305).

Multifunctionalized. Unless otherwise specified, the term "multifunctionalized" will be used to describe either mono- or multi-functionalized nanoparticles. Mono-functionalized particles shall refer to functionalized nanoparticles or agglomerations of nanoparticles onto which functional groups of a single type have been chemically bound. Multifunctionalized particles shall refer to nanoparticles or agglomerations of nanoparticles onto which at least two, and perhaps three or more, different types of functional groups have been chemically bound.

Resistant to Herbicide. Resistance to a dosage of herbicide refers to the ability of a plant to survive (i.e., the plant may not be killed) by that dosage of an active ingredient that would inhibit growth and/or result in the non-resistant plant from surviving. In some cases, tolerant plants may temporarily yellow or otherwise exhibit some herbicide-induced injury (e.g., excessive tillering and/or growth inhibition), but recover.

Stabilized. Stabilized refers to characteristics of a plant that are reproducibly passed from one generation to the next generation of inbred plants of the same variety.

Uptake. Uptake refers to the translocation of a particle or matrices, such as a nanoparticle (for example, gold, dendrimers, or quantum dots) across a cell wall or a cellular membrane, wherein the translocation does not occur solely as a result of momentum imparted to the particle by something other than the cell into which the particle is being uptaken. Non-limiting examples of devices or methods that cause translocation of a particle across a cell wall or a cell membrane solely as a result of momentum imparted to the particle are biolistic, gene gun, microinjection, and/or impalefection technologies.

Nucleic acid. The terms "nucleic acid," "polynucleotide," and "oligonucleotide" are used interchangeably and refer to a deoxyribonucleotide, ribonucleotide polymer, or other nucleotide or nucleoside polymer, in linear or circular conformation, and in either single- or double-stranded form. For the purposes of the present disclosure, these terms are not to be construed as limiting with respect to the length of a polymer. The terms may encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

Chromosome. A chromosome is a chromatin complex comprising all or a portion of the genome of a cell. The genome of a cell is often characterized by its karyotype, which is the collection of all the chromosomes that comprise the genome of the cell. The genome of a cell may comprise one or more chromosomes. An "episome" is a replicating nucleic acid, nucleoprotein complex or other structure comprising a nucleic acid that is not part of the chromosomal karyotype of a cell. Examples of episomes include plasmids and certain viral genomes. An "accessible region" is a site in cellular chromatin in which a target site present in the nucleic acid may be bound by an exogenous molecule that recognizes the target site. Without wishing to be bound by any particular theory, it is believed that an accessible region is one that is not packaged into a nucleosomal structure. The distinct structure of an accessible region may often be detected by its sensitivity to chemical and enzymatic probes, for example, nucleases. A "target site" or "target sequence" is a nucleic acid sequence that defines a portion of a nucleic acid to which a binding molecule will bind, provided sufficient conditions for binding exist. For example, the sequence 5"-GAATTC-3' is a target site for the EcoRI restriction endonuclease.

Gene. A gene, for the purposes of the present disclosure, includes a DNA region encoding a gene product, as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

Expression. The terms "expression" and "gene expression" are used interchangeably, and refer to the conversion of the information, contained in a gene, into a gene product. A gene product may be the direct transcriptional product of a gene (e.g., mRNA, tRNA, rRNA, antisense RNA, ribozyme, structural RNA or any other type of RNA) or a protein produced by translation of a mRNA. Gene products also include RNAs that are modified by processes such as capping, polyadenylation, methylation, and editing, and proteins modified by, for example, methylation, acetylation, phosphorylation, ubiquitination, ADP-ribosylation, myristilation, and glycosylation. "Modulation" of gene expression refers to a change in the activity of a gene. Modulation of expression may include, but is not limited to, gene activation and gene repression.

Protein. The terms "polypeptide," "peptide," and "protein" are used interchangeably to refer to a polymer of amino acid residues. The term also applies to amino acid polymers in which one or more amino acids are chemical analogues or modified derivatives of a corresponding naturally occurring amino acids.

Sequence. The term "sequence" refers to a nucleotide sequence of any length, which may be DNA or RNA, may be linear, circular or branched and may be either single-stranded or double-stranded. The term "donor sequence" refers to a nucleotide sequence that is inserted into a genome. A donor sequence may be of any length, for example, between 2 and 25,000 nucleotides in length (or any integer value therebetween or thereabove), preferably between about 100 and 5,000 nucleotides in length (or any integer therebetween), more preferably between about 200 and 2,500 nucleotides in length.

Homologous sequence. Homologous sequence refers to a first sequence that shares a degree of sequence identity with a second sequence, and whose sequence may be identical to that of the second sequence. A "homologous, non-identical sequence" refers to a first sequence that shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences may be any length and their degree of non-homology may be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs may be used.

Recombination. Recombination refers to a process of exchange of genetic information between two polynucleotides. For the purposes of this disclosure, "homologous recombination" (HR) refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer may involve mismatch correction of heteroduplex DNA that forms between the broken target and the donor, and/or "synthesis-dependent strand annealing" (SDSA), in which the donor is used to resynthesize genetic information that will become part of the target, and/or related processes. Such specialized HR often results in an alteration of the sequence of the target molecule, such that part or all of the sequence of the donor polynucleotide is incorporated into the target polynucleotide.

Cleavage. "Cleavage," "inducing a double-strand break," and "cut" are used interchangeably and refer to the breakage of the covalent backbone of a DNA molecule. Cleavage may be initiated by a variety of methods including, but not limited to, enzymatic or chemical hydrolysis of a phosphodiester bond. Both single-stranded cleavage and double-stranded cleavage are possible, and double-stranded cleavage may occur as a result of two distinct single-stranded cleavage events. DNA cleavage may result in the production of either blunt ends or staggered ends. In certain embodiments, fusion polypeptides are used for targeted double-stranded DNA cleavage. A "cleavage domain" comprises one or more polypeptide sequences, which possesses catalytic activity for DNA cleavage. A cleavage domain may be contained in a single polypeptide chain or cleavage activity may result from the association of two (or more) polypeptides. A "cleavage half-domain" is a polypeptide sequence that, in conjunction with a second polypeptide (either identical or different), forms a complex having cleavage activity (preferably double-strand cleavage activity). Double-strand break and double-stranded cleavage are used interchangeably.

Chromatin. Chromatin is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4, and linker DNA (of variable length depending on the organism) extends between nucleosome cores. A molecule of histone HZ is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

Binding. Binding refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}M^{-1}$ or lower. "Affinity" refers to the strength of binding: increased binding affinity being correlated with a lower $K_d$.

Operative linkage. The terms "operative linkage" and "operatively linked" (or "operably linked") are used interchangeably with reference to a juxtaposition of two or more components (such as sequence elements), in which the components are arranged, such that both components function normally and allow the possibility that at least one of the components may mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked with a coding sequence, but need not be directly adjacent to it. For example, an enhancer is a transcriptional regulatory sequence that is operatively linked to a coding sequence, even though they are not contiguous. With respect to fusion polypeptides, the term "operatively linked" may refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

Sequence Specific Nuclease (SSN). Sequence specific nucleases include several classes of bi-functional proteins that are capable of recognizing specific and unique nucleotide sequences (native or customized recognition sites) such as, but not limited to, meganucleases, leucine zippers and zinc finger proteins. Meganucleases represent a family of enzymes that can cleave double-stranded DNA with high-specificity in the presence of divalent metal ions (Ca, Mn, Mg). However, they differ from restriction endonucleases in their recognition properties and structures (Belfort et al. (1997) Nucleic Acids Res. 25:3379-88). In particular, where restriction enzymes recognize short nucleic acid sequences (3-8 bp), meganucleases recognize longer sequences (12-40 bp), which provides improved specificity to the targeting of DSB (Mueller et al. (1993) "Homing endonucleases." In *Nucleases, 2nd* Edition. Linn et al. (Eds), Cold Spring Harbor Laboratory Press, pp. 111-143.). Leucine zippers are a class of proteins that are involved in protein-protein interactions in many eukaryotic regulatory proteins that are important transcriptional factors associated with gene expression. The leucine zipper refers to a common structural motif shared in these transcriptional factors across several kingdoms including animals, plants, yeasts, etc. The leucine zipper is formed by two polypeptides (homodimer or heterodimer) that bind to specific DNA sequences in a manner where the leucine residues are evenly spaced through an α-helix, such that the leucine residues of the two polypeptides end up on the same face of the helix.

Zinc finger DNA binding protein. A zinc finger DNA binding protein (ZFP) may be a protein, or may be a polypeptide domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains may be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, e.g., U.S. Pat. Nos. 6,140,081; 6,453,242; 6,534, 261; and 6,785,613; see, also WO 98153058; WO 98153059; WO 98153060; WO 021016536 and WO 031016496; and U.S. Pat. Nos. 6,746,838; 6,866,997; and 7,030,215.

Genomic sequence. Genomic sequences include those present in chromosomes, episomes, organellar genomes (e.g., mitochondria, chloroplasts), artificial chromosomes and any other type of nucleic acid present in a cell such as, for example, amplified sequences double minute chromosomes and the genomes of endogenous or infecting bacteria and viruses. Genomic sequences may be normal (i.e., wild-type) or mutant; mutant sequences may comprise, for example, insertions, deletions, translocations, 25 rearrangements, and/or point mutations. A genomic sequence may also comprise one of a number of different alleles.

Plant cells. Plant cells include, but are not limited to, cells of monocotyledonous (monocots) or dicotyledonous (dicots) plants or algae or mosses. Non-limiting examples of monocots include cereal plants such as maize, rice, barley, oats, wheat, sorghum, rye, sugarmaye, pineapple, onion, banana, and coconut. Non-limiting examples of dicots include tobacco, tomato, sunflower, cotton, sugarbeet, potato, lettuce, melon, soybean, mayola (rapeseed), and alfalfa. Plant cells may be from any part of the plant and/or from any stage of plant development Region of interest. A region of interest is any region of nucleic acid polymer, such as, for example, a gene or a non-coding sequence within or adjacent to a gene, in which it is desirable to bind an exogenous molecule. Binding may be for the purposes of targeted DNA cleavage and/or targeted recombination. A region of interest may be present in a chromosome, an episome, an organellar genome (e.g., mitochondrial, chloroplast), plasmid, an infecting viral genome, or any other nucleotide sequence, for example. A region of interest may be within the coding region of a gene, within transcribed non-coding regions such as, for example, leader sequences, trailer sequences or introns, or within non-transcribed regions, either upstream or downstream of the coding region. A region of interest may be as small as a single nucleotide pair or up to 25,000 nucleotide pairs in length, or any integral value of nucleotide pairs.

According to embodiments of the invention, there may be provided a method of introducing a sequence-specific nuclease into a plant cell comprising a cell wall, the method comprising placing a sequence-specific nuclease coated nanoparticle in contact with the plant cell and allowing uptake across the plant cell wall. In particular aspects of the invention, the nanoparticle may be any nanoparticle and may reversibly or irreversibly contain, be coated with, or otherwise be bound to and/or carry a zinc finger nuclease, and/or a meganuclease. In certain embodiments, a zinc finger nuclease may be introduced to the nanoparticles before contact with a plant cell having a cell wall or concurrently with the introduction of the nanoparticle to a plant cell having a cell wall. Examples of nanoparticles that can be used in embodiments of the present invention include, but are not limited to, gold, quantum dots, gold coated nanoparticles, porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, semiconductor nanoparticles, quantum dots, nanomatrices, dendrimers and/or combinations thereof.

According to embodiments of the present invention, a plant cell having a cell wall may be any plant cell comprising an intact and whole cell wall. Embodiments of the invention may include cells comprising a cell wall from any tissue or wherever they are found, including but not limited to, in embryos, meristematic cells, callus, pollen, leaves, anthers, roots, root tips, flowers, seeds, pods, stems, suspension cultures, and tissue culture.

In particular embodiments of the invention, a SSN may be any ZFN that can be delivered to a plant cell according to the present invention. For example, ZFNs may comprise fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain may comprise one or more zinc fingers (e.g., 2, 3, 4, 5, 6, 7, 8, 9 or more zinc fingers), and may be engineered to bind to any region of interest. Thus, by identifying a target region of interest at which cleavage or recombination is desired, one may, according to the methods disclosed herein, construct one or more fusion proteins comprising a cleavage domain (or cleavage half-domain) and a zinc finger domain engineered to recognize a target sequence in the region of interest. The presence of such a fusion protein (or proteins) in a cell will result in binding of the fusion protein(s) to its (their) binding site(s) and cleavage within or near the region of interest. Moreover, if an exogenous polynucleotide homologous to the region of interest is also present in such a cell, homologous recombination occurs at a high rate between the double-strand break nucleotide sequence and the exogenous polynucleotide.

In particular embodiments, providing at least one SSN to a cell may comprise directly providing one or more copies of a SSN protein to the cell by way of a nanoparticle. In other embodiments, providing at least one SSN to a cell may comprise providing the cell with a nanoparticle that includes a nucleic acid encoding the SSN and allowing the cell to produce the SSN from the nucleic acid encoding it.

In other embodiments, one or more SSNs provided to the cell are capable of cleaving, individually, or in concert with other SSNs, at or near one or more regions of interest. In particular embodiments, one or more regions of interest may be within the coding sequence of a highly, more highly, very highly, or most highly expressed protein. In some embodiments, one or more regions of interest may be near and/or within a locus comprising a nucleotide sequence encoding a highly, more highly, very highly, or most highly expressed protein. In other embodiments, a nucleotide sequence may be double-strand break at a single region of interest. In further embodiments, a nucleotide sequence may be double-strand break at two or more regions of interest. In particular embodiments, one or more of the double-strand breaks may be located in the coding sequence of a highly, more highly, very highly, or most highly expressed protein. In other embodiments, one or more of the double-strand breaks may be near and/or within a locus comprising a nucleotide sequence encoding a highly, more highly, very highly, or most highly expressed protein.

In a particular embodiment where at least two double-strand breaks are made, repairing the double-strand breaks may comprise removing the material between the double-strand breaks and rejoining the ends of the nucleotide sequence so as to excise the sequences between the double-strand breaks. In embodiments, the excised sequences may, without limitation, comprise sequences encoding all or a portion of a nucleotide sequence encoding a highly, more highly, very highly, or most highly expressed protein. In further embodiments, the excised sequences may, without limitation, comprise regulatory sequences effecting the expression of a highly, more highly, very highly, or most highly expressed protein. In such embodiments, the expression of the highly, more highly, very highly, or most highly expressed protein is decreased relative to levels of expression prior to cleaving.

In alternative embodiments where at least two double-strand breaks are made, repairing the double-strand breaks may comprise removing the material between the double-strand breaks, replacing it with a donor sequence so as to substitute the sequences between the double-strand breaks with the donor sequence. In other embodiments, the removed sequences may, without limitation, comprise sequences encoding all or a portion of a nucleotide sequence encoding a highly, more highly, very highly, or most highly expressed protein. In further embodiments, the removed sequences may, without limitation, comprise regulatory sequences effecting the expression of a highly, more highly, very highly, or most highly expressed protein. In such embodiments, the expression of the highly, more highly, very highly, or most highly expressed protein is decreased relative to levels of expression prior to cleaving.

In embodiments where one double-strand break is made, repairing the double-strand break may comprise inserting a donor sequence into or across the double-strand break. In certain embodiments, the donor sequence may be inserted into the coding sequence of a highly, more highly, very highly, or most highly expressed protein. In embodiments, the insertion of such sequence may disrupt the transcription of the coding sequence of a highly, more highly, very highly, or most highly expressed protein through, by way of non-limiting example, the presence of an in-frame stop codon. In further embodiments, the donor may, without limitation, disrupt the function of regulatory sequences effecting the expression of a highly, more highly, very highly, or most highly expressed protein. In embodiments, the expression of a highly, more highly, very highly, or most highly expressed protein is decreased relative to levels of expression prior to cleaving.

In yet other embodiments, the donor sequence may encode a protein of interest. In further embodiments, expression of the protein of interest from the donor sequence may be controlled, regulated by, or operatively linked to regulatory sequences present in the donor sequence and/or regulatory sequences present in the sequence into which the donor sequence was inserted. In additional embodiments, a nucleic acid sequence encoding a protein of interest may be provided to the cell separate to or in conjunction with the donor sequence. In some embodiments, the donor sequence may be contained within the same nucleic acid molecule as the sequence encoding a protein of interest.

In other embodiments, the nucleotide sequence encoding a highly, more highly, very highly, or most highly expressed protein nucleotide sequence encoding a highly, more highly, very highly, or most highly expressed protein may be located in, by way of non-limiting example, a genome, a plasmid, a cosmid, artificial chromosome, episome, or other nucleotide structure in the cell.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. (1989) *Molecular Cloning: A Laboratory Manual, 2$^{nd}$ Edition*, Cold Spring Harbor Laboratory Press, NY; Sambrook et al. (2001) *Molecular Cloning: A Laboratory Manual, 3$^{rd}$ Edition*, Cold Spring Harbor Laboratory Press, NY; Ausubel et al. (1987) *Current Protocols in Molecular Biology*, John Wiley & Sons, NY (and periodic updates); the series, *Methods in Enzymology*, Academic Press, San Diego, Calif.; Wolffe (1998) *Chromatin Structure and Function, 3$^{rd}$ Edition*, Academic Press, San Diego, Calif.; Wassarman & Wolfe (eds.) (1999) "Chromatin." In *Methods in Enzymology*, Vol. 304, Academic Press, San Diego, Calif.; and Becker (ed.) (1999) "Chromatin Protocols." In *Methods in Molecular Biology*, Vol. 119, Humana Press, Totowa, N.J.

Nucleic Acid Delivery to Plant Cells

As noted above, DNA constructs may be introduced into (e.g., into the genome of) a desired plant host by a variety of conventional techniques. For reviews of such techniques, see, for example, Weissbach & Weissbach (1988) *Methods for Plant Molecular Biology*, Academic Press, NY, Section VIII, pp. 421-463; and Grierson & Corey (1988) *Plant Molecular Biology 2$^{nd}$ Edition*, Blackie, London, Ch. 7-9.

For example, the DNA construct may be introduced directly into the genomic DNA of the plant cell using techniques such as electroporation and microinjection of plant cell protoplasts, or the DNA constructs may be introduced directly to plant tissue using biolistic methods, such as DNA particle bombardment (see, e.g., Klein et al. (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transfection techniques, including disarming and use of binary vectors, are well described in the scientific literature. See, for example Horsch et al. (1984) Science 233:496-8, and Fraley et al. (1983) Proc. Natl. Acad. Sci. USA 80:4803.

In addition, gene transfer may be achieved using non-*Agrobacterium* bacteria, or viruses such as *Rhizobium* sp. NGR234, *Sinorhizoboium meliloti, Mesorhizobium loti*, potato virus X, cauliflower mosaic virus, cassava vein mosaic virus, and/or tobacco mosaic virus. See, e.g., Chung et al. (2006) Trends Plant Sci. 11(1):1-4.

Furthermore, cell-penetrating peptides fused to a nanoparticle or sequence-specific nuclease may be used to deliver nucleotide or protein sequences into a plant cell. The cell-penetrating peptide may be expressed, isolated, and functionalized with a nanoparticle, nucleotide sequence, or protein for delivery within plant cells. Cell-penetrating peptides capable of functionally delivering molecules into plant cells are known in the art and may include, but are not limited to: TAT (Chugh et al. (2008) FEBS 275:2403-14); R9 (Chang et al. (2005) Plant Cell Physiol. 46(3):482-8; and Chen et al. (2007) FEBS Lett. 581(9):1891-7); MPG (Ziegler et al. (2008) Adv. Drug Deliver. Rev. 6:580-97; and Morris et al. (1997) Nucleic Acids Res. 25:2730-6); PEP1 (Henriques et al. (2005) Biochemistry-US 44(3):10189-98); and plant-derived cell-penetrating peptides.

The virulence functions of the *Agrobacterium tumefaciens* host will direct the insertion of the construct and adjacent marker into the plant cell DNA when the cell is infected by the bacteria using binary T DNA vector (Bevan (1984) Nucleic Acids Res. 12:8711-21) or the co-cultivation procedure (Horsch et al. (1985) Science 227:1229-31). Generally, the *Agrobacterium* transfection system is used to engineer dicotyledonous plants (Bevan et al. (1982) Ann. Rev. Genet. 16:357-84; Rogers et al. (1986) Methods Enzymol. 118:627-41). The *Agrobacterium* transfection system may also be used to transform, as well as transfer, DNA to monocotyledonous plants and plant cells. See U.S. Pat. No. 5,591,616; Hemalsteen et al. (1984) EMBO J. 3:3039-41; Hooykass-Van Slogteren et al. (1984) Nature 311:763-4; Grimsley et al. (1987) Nature 325:1677-9; Boulton et al. (1989) Plant Mol. Biol. 12:31-40; and Gould et al. (1991) Plant Physiol. 95:426-34.

Alternative gene transfer and transfection methods include, but are not limited to, protoplast transfection through calcium-, polyethylene glycol-(PEG), or electroporation-mediated uptake of naked DNA (see Paszkowski et al. (1984) EMBO J. 3:2717-22, Potrykus et al. (1985) Mol. Gen. Genet. 199:169-77; From et al. (1985) Proc. Natl. Acad. Sci. USA 82:5824-8; and Shimamoto (1989) Nature 338:274-6) and electroporation of plant tissues (D'Halluin et al. (1992) Plant Cell 4:1495-505). Additional methods for plant cell transfection include microinjection, silicon carbide-mediated DNA uptake (Kaeppler et al. (1990) Plant Cell Rep. 9:415-8), and microprojectile bombardment (see Klein et al. (1988) Proc. Natl. Acad. Sci. USA 85:4305-9; and Gordon-Kim et al. (1990) Plant Cell 2:603-18).

The disclosed methods and compositions may be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules may be inserted, by targeted recombination, into regions of a plant genome favorable to their expression.

Transfected plant cells that are produced by any of the above transfection techniques may be cultured to regenerate a whole plant that possesses the transfected genotype and thus the desired phenotype. Such regeneration techniques rely on manipulation of certain phytohormones in a tissue culture growth medium, typically relying on a biocide and/or herbicide marker that has been introduced, together with the desired nucleotide sequences. Plant regeneration from cultured protoplasts is described in Evans et al. (1983) "Protoplasts Isolation and Culture." In *Handbook of Plant Cell Culture*, Macmillian Publishing Company, NY, pp. 124-76; and Binding (1985) *Regeneration of Plants, Plant Protoplasts*, CRC Press, Boca Raton, Fla., pp. 21-73. Regeneration may also be obtained from plant callus, explants, organs, pollens, embryos or parts thereof. Such regeneration techniques are described generally in Klee et al. (1987) Ann. Rev. Plant Physiol. 38:467-86.

Nucleic acids introduced into a plant cell may be used to confer desired traits on essentially any plant. A wide variety of plants and plant cell systems may be engineered for the desired physiological and agronomic characteristics described herein using the nucleic acid constructs of the present disclosure and the various transfection methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach, cabbage); flowering plants (e.g., *petunia*, rose, *chrysanthemum*), conifers and pine trees (e.g., pine fir, spruce); plants used in phytoremediation (e.g., heavy metal accumulating plants); oil crops (e.g., sunflower, rapeseed, soybean, palm) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Glycine, Gossypium, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it may be introduced into other plants by sexual crossing. Any of a number of standard breeding techniques may be used, depending upon the species to be crossed.

A transfected plant cell, callus, tissue or plant may be identified and isolated by selecting or screening the engineered plant material for traits encoded by the marker genes present on the transfecting DNA. For instance, selection may be performed by growing the engineered plant material on media containing an inhibitory amount of the antibiotic or herbicide to which the transfecting gene construct confers resistance. Further, transfected plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transfectants containing inserted gene constructs. These methods include, but are not limited to: 1) Southern analysis or PCR amplification for detecting and determining the structure of the recombinant DNA insert; 2) Northern blot, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins; and 5) Single Nucleotide Polymorphism detection technologies, invader assay, pyrosequencing, or solexa sequencing. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein may be observed by, for example, northern blots of the RNA (e.g., mRNA) isolated from the tissues of interest. Typically, if the amount of mRNA has increased, it may be assumed that the corresponding endogenous gene is being expressed at a greater rate than before. Other methods of measuring gene activity may be used. Different types of enzymatic assays may be used, depending on the substrate used and the method of detecting the increase or decrease of a reaction product or by-product. In addition, the levels of protein expressed may be measured immunochemically, i.e., ELISA, RIA, EIA and other antibody-based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above, wherein the progeny, clone, cell line or cell has the transgene or gene construct.

Applications

The disclosed methods and compositions for targeted cleavage may be used to induce mutations in a genomic sequence. Targeted cleavage may also be used to create gene knock-outs or gene knock-downs (e.g., functional genomics or target validation) and to facilitate targeted insertion of a sequence into a genome (i.e., sequence knock-in). Insertion may be by means of replacement of chromosomal sequences through, by way of non-limiting example, homologous recombination or by targeted integration, in which a new sequence (i.e., a sequence not present in the region of interest) is inserted at a predetermined target site. In certain examples, such new sequences may be flanked by sequences homologous to the region of interest in the chromosome. The same methods may also be used to replace a wild-type sequence with a mutant sequence or to convert one allele to a different allele.

Targeted cleavage of infecting or integrated plant pathogens may be used to treat pathogenic infections in a plant host, for example, by cleaving the genome of the pathogen such that its pathogenicity is reduced or eliminated. Additionally, targeted cleavage of genes encoding receptors for plant viruses may be used to block expression of such receptors, thereby preventing viral infection and/or viral spread in the plant.

Exemplary plant pathogens include, but are not limited to, plant viruses such as Alfarnoviruses, Alphacryptoviruses, Badnaviruses, Betaciyptoviruses, Bigeminiviruses, Bromoviruses, Bymoviruses, Capilloviruses, Carlaviruses, Carmoviruses, Cauliloviruses, Closteroviruses, Comoviruses, Cucurnoviruses, Cytorhabdoviruses, Dianthoviruses, Enamoviruses, Fabaviruses, Fijiviruses, Furoviruses, Hordeiviruses, Hybrigeminiviruses, Idaeoviruses, Ilawiruses, Ipomoviruses, Luteoviruses, Machlomoviruses, Macluraviruses, Marafiviruses, Mono geminiviruses, Nanaviruses, Necroviruses, Nepoviruses, Nucleorhabdoviruses, Oryzaviruses, Ourmiaviruses, Phytoreoviruses, Potexviruses, Potyviruses, Rymoviruses, satellite WAS, satelliviruses, Sequiviruses, Sobemoviruses, Tenuiviruses, Tobamoviruses, Tobraviruses, Tornbusviruses, Tospoviruses, Trichoviruses, Tymoviruses, Umbraviruses, Varicosaviruses and Waikaviruses; fungal pathogens such as smuts (e.g., *Ustilaginales*), rusts (*Uredinales*), ergots (*Clavicepts pupurea*) and mildew; molds (*Oomycetes*), such as *Phytophthora infestam* (potato blight); bacterial pathogens such as *Erwinia* (e.g., *E. herbicola*), *Pseudomonas* (e.g., *P. aeruginosa*, *P. syringae*, *P. fluorescens* and *P. putida*), *Ralstonia* (e.g., *R. solanacearum*), *Agrobacterium* and *Xanthomonas*; roundworms (*Nematoda*); and *Phytomyxea* (*Polymyxa* and *Plasmodiophora*).

The disclosed methods for targeted recombination production of a protein of interest may be used to replace any genomic sequence with a non-identical sequence. For example, a mutant genomic sequence may be replaced by its wild-type counterpart, thereby providing methods for treatment of plant diseases; provide resistance to plant pathogens; increase crop yields; etc. In like fashion, one allele of a gene may be replaced by a different allele using the methods of targeted recombination disclosed herein.

In many of these cases, a region of interest comprises a mutation, and the donor polynucleotide comprises the corresponding wild-type sequence. Similarly, a wild-type genomic sequence may be replaced by a mutant sequence, if such is desirable. For example, overexpression of an oncogene may be reversed either by mutating the gene or by replacing its control sequences with sequences that support a lower, non-pathologic level of expression. Indeed, any pathology dependent upon a particular genomic sequence, in any fashion, may be corrected or alleviated using the methods and compositions disclosed herein.

Targeted cleavage, insertion, excision, and/or recombination may also be used to alter noncoding sequences (e.g., regulatory sequences such as promoters, enhancers, initiators, terminators, splice sites) to alter the levels of expression of a gene product. Such methods may be used, for example, for therapeutic purposes, functional genomics and/or target validation studies.

Targeted modification of chromatin structure may be used to facilitate the binding of fusion proteins to cellular chromatin. In additional embodiments, one or more fusions between a zinc finger binding domain and a recombinase (or functional fragment thereof) may be used, in addition to or instead of the zinc finger-cleavage domain fusions disclosed herein, to facilitate targeted recombination. See, for example, co-owned U.S. Pat. No. 6,534,261 and Akopian et al. (2003) Proc. Natl. Acad. Sci. USA 100: 8688-91. In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

Furthermore, as disclosed above, the methods and compositions set forth herein may be used for targeted integration of exogenous sequences into a region of interest in the genome of a cell, for example, in which cleavage enhances insertion via homology-dependent mechanisms (e.g., insertion of a donor sequence comprising an exogenous sequence together with one or more sequences that are either identical, or homologous but non-identical, with a predetermined genomic sequence (i.e., a target site).

The donor sequence may contain sufficient homology in the regions flanking the exogenous sequence to support homology-directed repair of a double-strand break in a genomic sequence, thereby inserting the exogenous sequence at the genomic target site. Therefore, the donor nucleic acid may be of any size sufficient to support integration of the exogenous sequence by homology-dependent repair mechanisms (e.g., homologous recombination). Without wishing to be bound by any particular theory, the regions of homology flanking the exogenous sequence are thought to provide the broken chromosome ends with a template for re-synthesis of the genetic information at the site of the double-stranded break. In certain embodiments, two of the identical sequences or two of the homologous but nonidentical sequences (or one of each) are present, flanking the exogenous sequence. An exogenous sequence (or exogenous nucleic acid or exogenous polynucleotide) is one that contains a nucleotide sequence that is not normally present in the region of interest.

Exemplary exogenous sequences include, but are not limited to, cDNAs, promoter sequences, enhancer sequences, epitope tags, marker genes, cleavage enzyme recognition sites and various types of expression constructs. See, for example, U.S. Pat. No. 6,833,252. Additional exemplary homing endonucleases include I-CeuI, PI-PspI, PI-Sce, I-SceIV, I-CsmI, I-PanI, I-SceII, I-PpoI, I-SceIII, ICreI, I-TevI, I-TevII and I-TaiIII. Their recognition sequences are known. See also U.S. Pat. No. 5,420,032; Belfort et al. (1997) Nucleic Acids Res. 25:3379-88; Dujon et al. (1989) Gene 82:115-8; Perler et al. (1994) Nucleic Acids Res. 22:1125-7; Jasin (1996) Trends Genet. 12:224-8; Gimble et al. (1996) J. Mol. Biol. 263:163-80; Argast et al. (1998) J. Mol. Biol. 280:345-53; and the New England Biolabs catalogue.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins that mediate enhanced cell growth and/or gene amplification (e.g., dihydrofolate reductase). Exemplary marker genes thus include, but are not limited to, β-glucuronidase (GUS), phosphinothricin N-acetyl transferase (PAT, BAR), neomycin phosphotransferase, p-lactamase, catechol dioxygenase, a-amylase, tyrosinase, P-galactosidase, luciferase, aequorin, EPSP synthase, nitrilase, acetolactate synthase (ALS), dihydrofolate reductase (DHFR), dalapon dehalogenase and anthranilate synthase. In certain embodiments, targeted integration is used to insert a RNA expression construct, e.g., sequences responsible for regulated expression of micro RNA or siRNA. Promoters, enhancers and additional transcription regulatory sequences, as described above, may also be incorporated in a RNA expression construct.

Conventional Transformation uses random integration of foreign DNA to produce modified transgenic crop plant with the trait of choice that is subjected to tight restrictions in some foreign markets. In addition, undesirable outcomes also arise from the method of DNA introduction or from the random insertion of the transgene into sensitive areas of the genome, often many times per genome. In particular, the effects of imprecise insertion may not manifest themselves in early generations since different DNA error-checking mechanisms are activated during growth, reproduction, embryogenesis, and development. These outcomes impact the time and dollar costs of any transgenic program in agricultural biotechnology. However, in a recent Dow AgroSciences invention (WO/2008/021207), a method for precision insertion of transgenes is described via Zinc Finger Nuclease (ZFN)-mediated homologous recombination. Conversely, where the ZFN protein can be expressed and purified outside the target organism and then delivered into target plant cells, surgically specific mutation/gene knockout may be induced via non-homologous end joining (NHEJ). Thus, the present invention can produce a non-transgenic genetically modified plant that would bypass restrictions on transgenic crops and process of targeted gene editing will be possible without requiring a transgenic approach.

Methods for the heterologous expression of sequence-specific nuclease proteins, such as ZFN proteins, are known within the art. Applicable expression systems include, but are not limited to: the use of an in vitro system such as wheat germ cell-free system (see U.S. Pat. No. 7,235,382, herein incorporated by reference); the *Pseudomonas fluorescens* expression system (Madduri et al., (2007) Protein Expres. Purif. 55(2):352-60); and the *Pichia* protein expression system (see U.S. Pat. Nos. 4,683,293; 4,808,537; 4,812,405; 4,818,700; 4,837,148; 4,855,231; 4,857,467; 4,879,231; 4,882,279; 4,885,242; 4,895,800; 4,929,555; 5,002,876; 5,004,688; 5,032,516; 5,122,465; 5,135,868; 5,166,329, herein incorporated by reference).

Particular embodiments of the present invention include an exogenously expressed functional ZFN conjugated to nanoparticles (NP) and delivered via NP-mediated smart and stealthy delivery method into the intact plant cells to induce the double-strand break and the restoration of the functionality of the disrupted gene by NHEJ. In other embodiments, the functional ZFN conjugated to NP is delivered with a donor fragment of DNA via NP-mediated smart and stealthy delivery method. Wherein the ZFN cleaves a specific sequence within the genome and the donor DNA is integrated into this locus via homologous recombination. Strategies to link a protein to the NP have taken four main approaches: (1) electrostatic adsorption, (2) conjugation to the ligand on the NP surface, (3) conjugation to a small cofactor molecule that the protein can recognize and bind, and (4) direct conjugation to the NP surface (Aubin-Tam and Hamad-Schifferli, 2008). Other strategies are described in the review of Medintz et al. Issues involved in these labeling strategies include sterics, or whether the protein can "get past" the ligand to the NP surface or the relevant linking group. A choice of chemistries that result in a specific link (i.e., do not cause extensive cross-linking) and are stable for the desired purpose are also necessary considerations. ZFN peptide needs to be functionalized under high DDT concentration and in the presence of zinc ions. In order to keep the stability of the conjugates, the functionalization will be done according to the conjugation procedure described in Oh et al. 2010.

The invention is further described with the aid of the following illustrative examples.

EXAMPLES

Example 1: Production of Sequence-Specific Nucleases (SSNs) Through In Vitro Translation or Bacterial Expression SSNs (IL1-LO/Fok1, IL1-43/Fok1, IL1-8/Fok1 and I-SceI) are engineered and PCR amplified from plasmids containing the SSNs, attaching restriction enzyme sites and 6x histidine tags. The PCR product is inserted into TOPO vector pCR2.1 for cloning and sequencing.ABased on gene fragments that contain the SSN encoding sequence are removed from the plasmid via restriction digestion and ligated into compatible restriction sites of the expression vector pET15b. These samples are transformed into BL21 expression competent *E. coli* cells along with pDAB4883. For effective expression, SSN protein damage is reduced in BL21 *E. coli* DNA by transforming BL21 with the plasmid pDAB4883 consisting of pCOT4 expression plasmid containing a ligase gene downstream of a promoter that is also induced by IPTG (isopropyl-beta-D-thiogalactopyranoside). This helps repair any damage done by the SSNs to the genome of the BL21 cells during over expression.

The ligase gene-pCOT4 construct and the SSN-pET15b constructs are co-transformed into the same BL21 expression cells. The cultures of the transgenic BL21 are grown in 50 mL LB media with chloramphenicol, carbenicillin, and ZnCl$_2$ and incubated at 37° C. until OD$_{600\,nm}$ reaches 0.5. Expression is induced with various concentrations of IPTG (0.1-0.7 mM), incubation is at various temperatures (16-28° C.) and analysis is via SDS-PAGE and Western Blot for detection of the presence of the SSN protein. Thus, IL1-LO/Fok1, IL1-43/Fok1, IL1-8/Fok1 and I-SceI are expressed in *E. coli* cells and Ni-NTA-purified. Following purification, SSN function is demonstrated based on the ability to release a specific fragment from an expression plasmid.

Alternatively, the sequence-specific nucleases are expressed via in vitro translation. A commercial kit, TNT®, from Promega provides an efficient and convenient process for expressing protein. Circular plasmids containing sequence-specific nuclease genes cloned downstream from either the T7 or SP6 RNA polymerase promoters are expressed in vitro by protein-expressing enzymes supplied with the kit. Synthesized proteins are produced in a 50 µL reaction within 60-90 minutes following the manufacturer's protocol. Additional commercial kits are available for in vitro translation of protein, additional kits that may be used include: ActivePro™ from Ambion, PROTEINscript™ II from Ambion, PURExpress™ from New England Biolabs, in addition to other commercially available kits.

Figure 1:
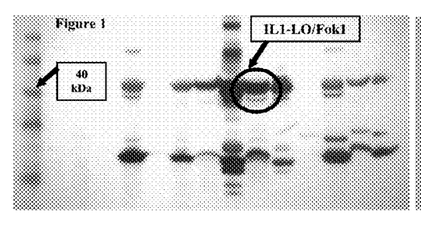
FIGS. 1 and 2 show *E. coli* expression of histidine-tagged (1) and non-histidine-tagged (2) ZFN-IL1 FokI, respectively.
Figure 2:
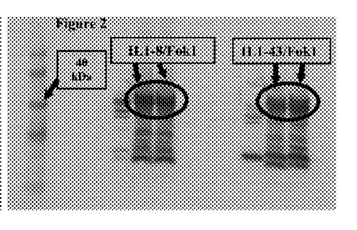

FIGS. 1 and 2 show *E. coli* expression of histidine-tagged (1) and non-histidine tagged (2) SSN, ZFN-IL1Fok1. In vitro-expressed ZFN-IL1Fok1 releases a well defined ZFN-binding site-flanked fragment from the plasmid. Thus, both *E. coli* and in-vitro expressed SSNs are useful for the efficient and specific digestion of target DNA molecules, and they are used alternately throughout this investigation.

Figure 4:
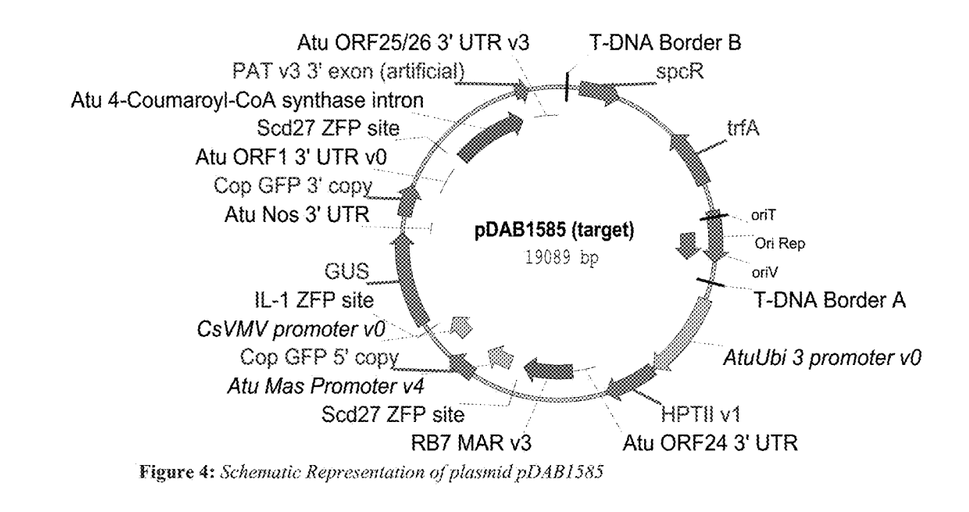
FIG. 4 shows a schematic representation of plasmid pDAB1585.

Proteins expressed from cloned SSN genes are shown to be functional (i.e., in cleaving the donor DNA). For example, plasmid pDAB1585 (shown in FIG. 4) is treated with the ZFN-IL1Fok1. The digested plasmid DNA is linearized. The linearized fragment from the ZFN-IL1Fok1-digested plasmid is then purified from the gel and is self-ligated using an overnight in vitro ligation procedure. The ligation product is transferred into chemically competent DH5α *E. coli* cells. Several recombinant colonies are recovered and analyzed by both restriction pattern analysis and DNA sequencing, demonstrating that pDAB1585 digests as expected.

Figure 3:
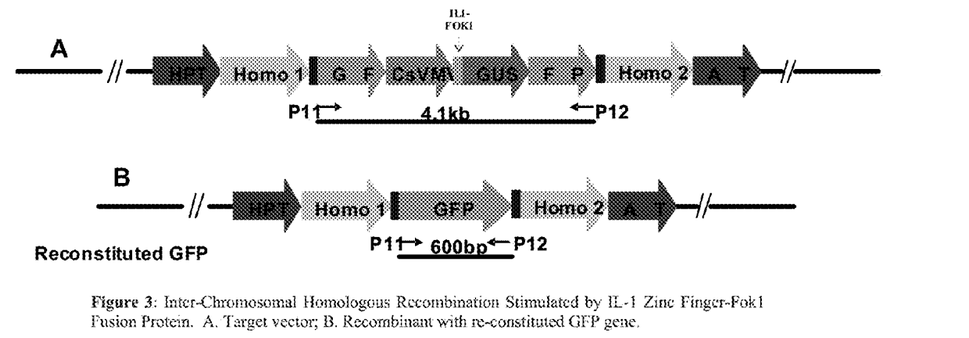
FIG. 3 shows inter-chromosomal homologous recombination stimulated by IL-1 zinc finger-Fok1 fusion protein, with A representing the target vector and B representing a recombinant vector with re-constituted GFP gene.
Figure 6:
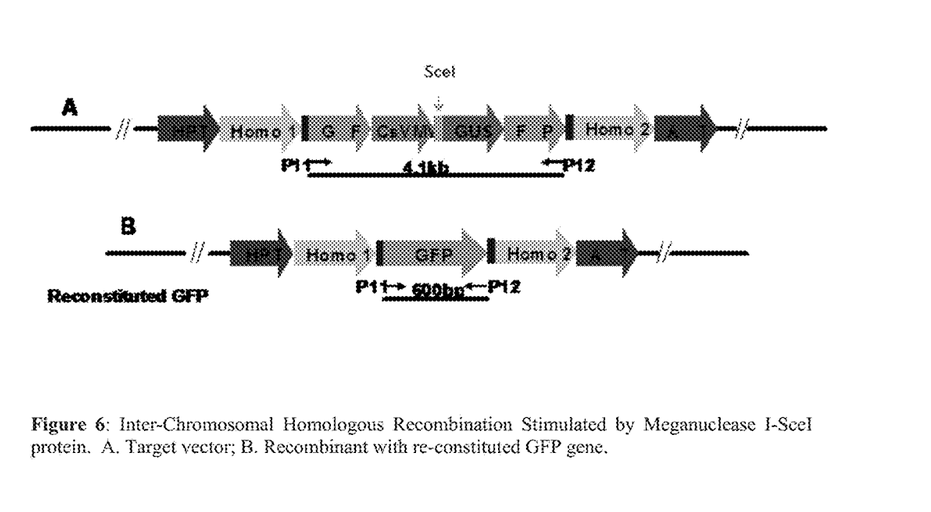
FIG. 6 shows inter-chromosomal homologous recombination stimulated by meganuclease I-SceI protein, with A representing the target vector and B representing a recombinant vector with re-constituted GFP gene.

Example 2: Production of Target Cell Cultures with SSN Binding Sites Flanked by GFP Reporter Gene Fragments Target sequences consist of two Green Fluorescent Protein (gfp) gene fragments (Evrogen Joint Stock Company, Moscow, Russia) flanking a β-glucuronidase (uidA) expression cassette. In one target construct, a ZFN binding site with recognition sequences consisting of inverted repeats to which zinc finger-FokI fusion proteins can bind as homodimers (FIG. 3) is integrated into the target construct. The binding site contains four tandem repeats of the recognition sequence of IL1-FokI fusion protein so that each binding site is ~200 bp in size to ensure that the recognition sequences are accessible to the zinc finger-Fok1 fusion protein in the complex chromatin environment. In a second construct, an I-SceI binding site is integrated into the target construct (FIG. 6). In each target construct, the binding sites are fused with the uidA coding sequence at the N-terminus. The 5' and 3' gfp gene fragments overlap by 540 bp. These overlapping sequences provide homology within the target sequences and a stop codon is inserted at the 3' end of the 5' gfp fragment to ensure no functional gfp transcription from the target sequence.

Figure 7:
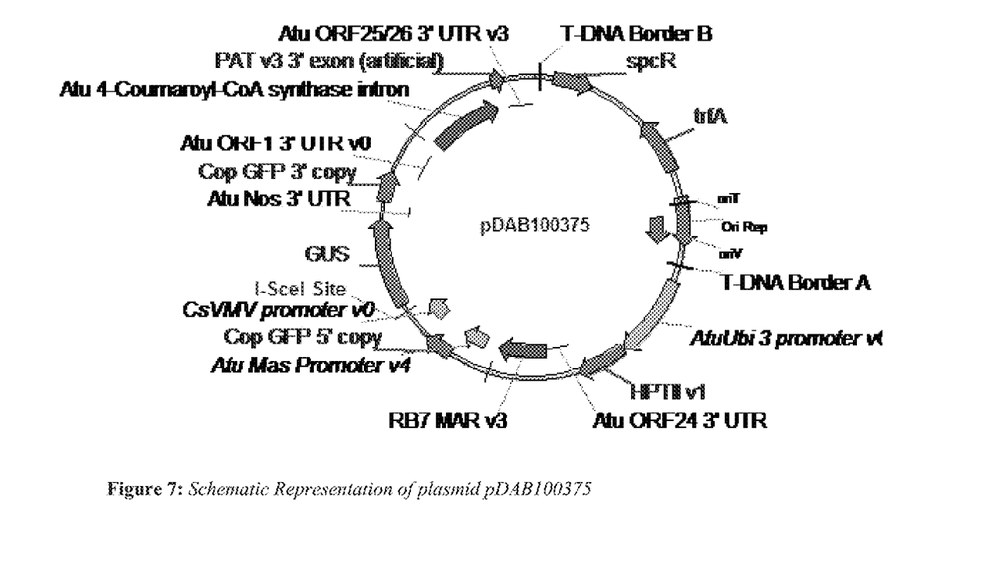
FIG. 7 shows a schematic representation of plasmid pDAB100375.

Target sequences are stably integrated into BY2 tobacco cell suspension cultures using *Agrobacterium* transformation. BY2 cultures (obtained from Jun Ueki of Japan Tobacco, Iwata, Shizuoka, Japan) are maintained in media containing LS basal salts (PhytoTechnology Labs, Shawnee Mission, Kans., #L689), 170 mg/L KH$_2$PO$_4$, 30 g/L sucrose, 0.2 mg/L 2,4-D and 0.6 mg/L thiamine-HCL at a pH of 6.0. The BY2 cells are sub-cultured every seven days by adding 0.25 mL PCV to 50 mL of LS-based medium maintained in 250-mL flasks on a rotary shaker at 25° C. and 125 RPM. In order to generate transgenic BY2 cell cultures with integrated target sequences, a flask of a four-day post subculture suspension is divided into 10-12 four mL aliquots, which are co-cultivated in 100×25 mm Petri dishes with 100 µL *Agrobacterium* strain LBA4404 harboring either pZFN-TARGET pDAB1585 (FIG. 4) or pI-SceI-TARGET pDAB100375 (FIG. 7) grown overnight to an OD$_{600}$~1.5. Dishes are wrapped with NESCOFILM® (Azwell Inc., Osaka, Japan) and incubate at 25° C. without shaking for three days after which excess liquid is removed and replaced with 11 mL of LS medium containing 500 mg/L carbenicillin. Following re-suspension of the tobacco cells, 1 mL suspension is dispensed onto 100×25 mm plates of LS medium containing 500 mg/L carbenicillin and 200 mg/L hygromycin solidified with 8 g/L TC agar (PhytoTechnology, Shawnee Mission, Kans.). The plates incubate unwrapped at 28° C. in the dark. This results in 120-144 selection plates for a single treatment. Individual hygromycin-resistant isolates appear at 10-14 days after plating and are transferred to individual 60×20 mm plates (one isolate per plate) where they are maintained under selection as callus on a 14-day sub-culture schedule until needed for analysis and subsequent re-transformation experiments.

Hygromycin-resistant, transgenic cell cultures containing a single, full-length integrated copy of the target sequence, are selected and used to re-initiate suspension cultures by placing ~250-500 mg of callus tissue into 40-50 mL of LS basal medium containing 100 mg/L hygromycin and sub-culturing every seven days, as described above.

Both cell clusters and single cells (produced as described in the DAS single cell patent application, WO/2008/083233) are used in the experiments. Three to four days prior to experiments, a one-week-old suspension culture is subcultured to fresh medium by transfer of 2 mL of BY2 suspension aggregates into 40 mL of LSBY2 medium containing stock concentration of 4-chloro-1,5-diphenyl-1H-pyrazol-3-yloxy)-acetic acid ethyl ester (as described in patent WO/2008/083233) 1-3% Glycerol, and 0.05-0.1% (v/v) DMSO in a—250 mL flask. Single cells are collected either at 3.5 days or 7 days after the treatment to induce single cells. The BY2 single cells are processed through a Flow-cytometer to determine the viability of the cells and also evaluate, via confocal microscopy, the stability of cells. The stability is detected by observing the level of background fluorescence, if any. A small percentage of cells show background fluorescence that matches the dead cells, indicating that the background fluorescence is from the cells that underwent necrosis. Both the single cells and the regular suspension aggregates are used in the experiments after testing for the background fluorescence.

Example 3: Coating Nanoparticles (NP) with SSNs for Delivery into Plant Cells

Gold colloids of 150 nm diameter in size (BBI International, GC150), 5-((2-(and-3)-S(acetylmercapto)succinoyl) amino) fluorescein (SAMSA fluorescein: Invitrogen, A-685), nanoparticles of size 80 and 90 nm carboxylic acid multifunctionalized gold colloids (TedPella, 32019), Sulfo-NHS (N-hydroxysulfosuccinimide), EDC (1-ethyl-3-[3-dimethylaminopropyl]carbodiimide hydrochloride), (Pierce Biotechnology, 24510, 22980), MES (2-[N-morpholino]ethane sulfonic acid) (Fisher Scientific, AC32776-1000), phosphate-buffered saline buffer packets (Sigma, P5368-10PAK), histidine-tagged GFP (Evrogen, Excitation max—482 nm, Emission max—502 nm, FP611), turbo YFP (Evrogen, Excitation max—525 nm, Emission max—538 nm, FP611), Propidium iodide (Sigma-P4864), fluorescein diacetate (Sigma, F7378) are types of multifunctionalized NP that are coated with SSNs and used for delivery into the target cell cultures.

(i) Preparation of Nanoparticle Conjugates (a) Synthesis of gold-fluorescein conjugate without SSNs for control treatments: gold-fluorescein conjugate is prepared by a method described previously (Cannone et al. (2006)) for delivering and tracking the particles in BY2 cluster or single cells without SSNs. One (1) mg of SAMSA fluorescein is dissolved in 100 µl of 0.1 M NaOH and vortexed for 15 minutes to remove the acetyl group protecting the thiol. The activated SAMSA is then mixed with 100 µl of 150 nm gold colloids (~109 particles/mL). This solution is then incubated for one hour to ensure the completion of the reaction. Then, 50 µl of 1 M HCl is added to neutralize the solution. The solution is centrifuged at 3000 RPM for 30 minutes and the supernatant is removed. The obtained yellow pellet is re-suspended in 200 µL, of 0.1 M PBS, resulting in an orange colored solution. This purification step is repeated two times to ensure removal of free SAMSA fluorescein. The mode of attachment of SAMSA to gold is mainly via thiol bonding. Due to the significant electrostatic repulsion (SAMSA is dianionic at pH>7), SAMSA is thought to lie perpendicular to the gold colloidal surface (Cannone et al. (2006)). Such NP are used to track the entry of the number of such fluorescing particle entering into the cells as a measure of indication of cell amenability in the given conditions.

(b) Synthesis of gold nanoparticle (GNP) coated with SSN: GNP-SSN conjugates are synthesized using a slightly modified protocol described by Grabarek and Gergely (1990). 0.25 mL of 20-150 nm carboxyl acid multifunctionalized gold colloidal solution (~109 particles/mL) is centrifuged at 3000 RPM for 10 minutes. After discarding the supernatant, the red pellet is suspended in 1 mL of activation buffer (0.1 M MES, 0.5 M NaCl, pH 6.0). Thereafter, 0.4 mg EDC and 1.1 mg of sulfo-NHS is added to this solution and vortexed for 15 minutes at room temperature. Then, 9 µL, of ZFN-IL1Fok1 is added and the resulting solution is incubated for up to two hours in the dark at room temperature in order for the protein and gold to react completely. The ratio of gold colloids and protein used in this reaction is determined by finding the number of carboxylic acids present on gold colloids. First, the number of carboxylic groups present on one gold colloid is calculated by dividing the surface area of one gold particle (sphere assumption) by the surface occupied by one carboxylic group (0.20 $nm^2$ (Kimura et al. (2002))). Then, this result is multiplied by total number of gold colloids present to obtain total number of carboxylic groups present in the entire gold colloidal solution. This is equated with the number of amino groups present in given amount of protein. The gold colloids attach to protein via the formation of an amide bond between carboxylic acid present on the gold colloid and the amino group present on protein (Grabarek and Gergely (1990)). There are roughly 127,285 protein molecules tethered to one gold nanoparticle.

(ii) Cell Treatment a) Time course of gold uptake and cell viability: The following samples are prepared in 24-well sterile plates: (i) 500 µl of target suspension cluster or single cells (control); (ii) 500 µl, of BY2 suspension cluster or single cells+20 µl of GNP+25 µl of Fluorescein diacetate (FDA)+25 µl of propidium iodide; and (iii) other treatments include 40, 60, 80 µl of GNP alone and in combination of ZFN-IL1Fok1 with the cells and cell viability stains. Treated samples are examined under fluorescence microscope at 5, 20, 120 minutes and finally after 24-48 hours to confirm the viability of the cells.

b) Gold-SAMSA fluorescein treatments: The following samples are prepared in 24-well sterile plates before the experiments: (i) 500 µl of target suspension cluster or single cells (control); (ii) 500 µl of target suspension cluster or single cells+20 µl of SAMSA-fluorescein (control); and (iii) target suspension cluster or single cells+20 µl of GNP-SAMSA-fluorescein are treated and the suspensions are incubated for 20 minutes in dark at room temperature to confirm the entry of particles.

c) GNP coated (e.g., tagged) ZFN-IL1Fok1 treatments: The following samples are prepared in 24-well sterile plates prior to the cell or suspension cluster treatments: (i) 500 µL target suspension cluster or single cells (control); (ii) 500 µL target suspension cluster or single cells+9-20 µL of ZFN (control); and (iii) 500 µl of single cells+10-40 µL of GNP-coated (e.g., tagged) ZFN-IL1Fok1. The treated cells and clusters are incubated for up to two hours in dark at room temperature before the experiments.

Figure 5:
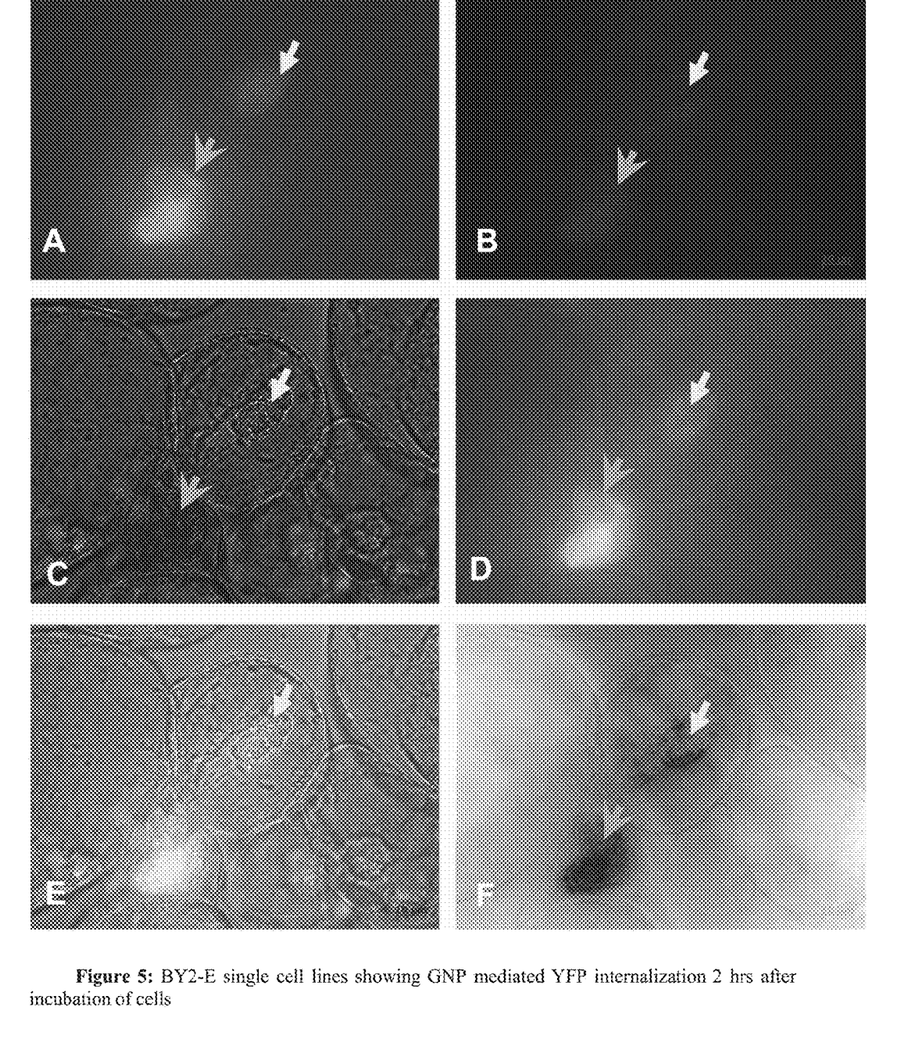
FIG. 5 shows BY2-E single cell lines showing GNP-mediated YFP internalization two hours after incubation of cells; Panels A (FITC), B (Rhodamine), C (DIC), D (A+B), E (A+B+C), and F (Reflectance image inverted): YIP internalization as observed through fluorescence microscopy.

Control treatments using GFP/YFP tethered GNPs are included in all experiments to ensure non-invasive penetration and the timing of optimum entry, which is used as guidance in the experiments (see FIG. 5). In addition, fusion cell-penetrating peptides (CPPs) are fused (e.g., multifunctionalized) to NP to track the real time entry of particles into the target suspension clusters and single cells.

Example 4: Synthesis of Quantum Dot (QD)-Tagged SSN Conjugates

Luminescent semiconductor nanocrystals QDs provide a powerful prototypical example with many demonstrated biological applications (Thermes et al. (2002); Windbichler et al. (2007); Fajardo-Sanchez et al. (2008); Arnould et al. (2006)). Their utility is derived from the combination of unique photophysical characteristics and sizes comparable to that of a large protein. The hydrodynamic radius of hydrophilic CdSe—ZnS QDs varies from ~5 nm (for nanocrystals cap exchanged with molecular ligands) to ~20 nm (for nanocrystals encapsulated within block copolymers) (Smith et al. (2006)). A single QD is conjugated with several biomolecules (such as antibodies, peptides, DNA) to provide coated QD bioconjugates with enhanced avidity.

Use of ZFN-IL1Fok1 conjugated (e.g., coated) to hydrophilic QDs as an alternate strategy to facilitate their intracellular uptake and delivery to the appropriate target DNA site is described in this example. The method generally follows the procedure for the internalization of QD-protein cargos into live cells as described in the DAS patent application 65502.

(i) QD synthesis: CdSe—ZnS core-shell QDs with emission maxima centered at 510 and 540 nm are synthesized using stepwise reactions of organometallic precursors in hot coordinating solvent mixtures following the procedures described (Lu et al. (2007); Doyon et al. (2006); Collins et al. (2003); Lanio et al. (2000)). The nanocrystals are multifunctionalized and made hydrophilic by exchanging the native capping shell, composed primarily of trioctyl phosphine and trioctyl phosphine oxide (TOP/TOPO), with bifunctional ligands as previously described (Lie et al. (2002); Mani et al. (2005); Desjarlais and Berg (1993)). Two sets of hydrophilic QDs are used: (1) nanocrystals capped with only dihydrolipoic acid; and (2) nanocrystals capped with a mixture of poly(ethylene glycol)-appended dihydrolipoic acid (PEG Mw≅600, DHLA-PEG) and biotin-terminated DHLA-poly(ethylene glycol) (PEG Mw≅400, DHLA-PEG-biotin) with a 9:1 molar ratio of the ligands. These are referred to as DHLA-QDs and DHLA-PEG-biotin-QDs, respectively.

(ii) Self-Assembly of Quantum Dot Bioconjugates: To self-assemble QD-ZFN-IL1Fok1 conjugates at the desired valence, His-ZFN at the appropriate molar ratios are added to 0.3 µM of 510-nm emitting DHLA-capped QDs in 10 mM Tris-Cl pH 8 buffer and incubated at room temperature for 30 minutes. Similarly, b-PE-Streptavidin is added to 0.3 µM of 540-nm emitting QDs (capped with DHLA-PEG:DHLA-PEG-biotin 9:1 ratio) in phosphate-buffered saline (137 mM NaCl, 10 mM phosphate, 2.7 mM KCl, pH 7.4, PBS) and incubated at 4° C. overnight; conjugate formation in this case is driven by Streptavidin-biotin interactions. Conjugates are characterized using gel electrophoresis, where changes in the electrophoretic mobility of QDs assembled with either His-appended ZFN or Streptavidin-labeled b-PE are monitored. Samples are diluted in 1×TBE buffer (0.09 M Tris, 0.002 M Na2-EDTA 0.09 M Boric acid pH 8.3) and run on 1% or 2% agarose gels for QD-b-PE and YFP conjugates, respectively. In particular, the effects of varying the number of ZFN-IL1Fok1 molecules per QD bioconjugate are monitored if they are fused to fluorescent proteins for tracking Gel images are collected by exciting the QD and/or protein and capturing fluorescence images of the separated bands within the gels. Conjugate formation is confirmed by monitoring changes in the energy transfer between the QDs and fluorescent proteins upon self-assembly. Fluorescent spectra are collected on a Tecan Safire Dual Monochromator Multifunction Microtiter Plate Reader (Tecan, Research Triangle Park, N.C.) using 325 nm excitation. For intracellular delivery and imaging experiments, QDs are self-assembled with a mixture of the ZFN-IL1Fok1 at a nominal ZFN:QD molar ratio.

(iii) Intracellular Uptake of Quantum Dot—Fluorescent Protein Conjugates: Cellular internalization experiments are performed in sterile conditions, as previously described. QD bioconjugates are diluted into complete culture medium, added to the cell culture, and incubated at 37° C. for one hour at 40-150 µg/mL. Mixed surface QD coated conjugates consisting of either 1:5 or 1:10 QD/ZFN and QD/b-PE with assembly valence of 1:1 to 1:2.5, together with CPP at 50 CPPs per QD, are incubated with the cell cultures at different QD conjugate concentrations. Excess unbound QD conjugates are removed by washing the culture at least three times with PBS or cell culture medium. Cells are then fixed in 3.7% paraformaldehyde for 10 minutes at room temperature, washed twice with PBS, and mounted in ProLong Antifade mounting media containing DAPI dye (Invitrogen) for nuclear staining Epifluorescence image collection is carried out using a Leica microscope. Side-by-side split fluorescence images are collected and quantitated using a Dual-View™ system equipped with a 565 nm dichroic filter. For 510 nm QD-YFP/ZFN cellular imaging, samples are excited at 488 nm and emissions are collected/separated with the 565 nm dichroic and deconvoluted. QD fluorescence is collected at λ<565 nm and the YFP fluorescent tail collected at λ>565 nm. YFP leakage into the QD window is subtracted as part of the deconvolution. The 540 nm QDs and b-PE are excited at 488 nm and their respective emissions are separated with the 565 nm dichroic filter and deconvoluted. DAPI fluorescence is excited using a Xe lamp and emission collected using a DAPI cube (D350/50× for excitation, dichroic 400DCLP, D460/50m for detection). AF647-TF is excited using the Xe lamp and fluorescence detected using a Cy5 cube (excitation HQ620/60×, dichroic Q660LP, emission HQ700/75m). Both excitation/detection cubes are provided by Chroma Technology. Differential interference contrast (DIC) images are collected using a bright light source.

(iv) ZFN-IL1Fok1 coated QDs confirmation: His interactions occur directly with the Zn-rich inorganic surface of the nanocrystals. Engineering ZFN-IL1Fok1 with an N-terminus bearing two-(His)6 sequences separated by a small spacer and CPP having an N-terminal (His)8 sequence permits the formation of tight QD-protein/peptide complexes. Biotin-avidin binding is a ubiquitous bioconjugation strategy known in the art for its strong interaction (KD~$10^{-15}$ M). Using QDs surface-capped with a mixture of hydroxyl- and biotin-terminated PEG (DHLA-PEG-biotin-QDs) allows for easy conjugation (e.g., coating) to commercially available b-PE-Streptavidin.

(v) Intracellular Delivery of QD-ZFN-IL1Fok1 Conjugates: To verify that uptake of multifunctionalized (e.g., surface functionalized) QDs coated with YFP/ZFN-IL1Fok1 cargo is mediated by the presence of CPP on the nanocrystal surface, target BY2 cell lines are separately incubated with three types of conjugate: QD-CPP conjugates (10-100 CPP per QD), QD-ZFN-IL1Fok1/CPP, and QDs assembled with a mixture of ZFN-IL1Fok1 and CPP (QD-ZFN-IL1Fok1-CPP with ~10 ZFN-IL1Fok1 and ~50 CPP per conjugate). Cells are incubated with solutions of 510-nm emitting QD conjugates (at ~75 nM concentration), rinsed to remove any unbound materials, and subsequently imaged using epifluorescence microscopy. Cells are also counter-stained with DAPI to allow visualization of the nuclei and endosomes, respectively. When additional CPP is present on the QD surface (mixed surface QD-ZFN-IL1Fok1-CPP conjugates), a substantial intracellular uptake of conjugates takes place as indicated by the pronounced fluorescence intensity measured for both sets of cells. Furthermore, images collected for both cultures show that there is a nearly complete overlap between the fluorescence patterns of the QD and ZFN-IL1Fok1/YFP. Evaluation of the staining patterns and co-localization pattern indicates a perinuclear distribution, and are predominantly confined within endosomal compartments. The efficient internalization of QD conjugates by the cell lines in the presence of CPP demonstrates that CPP facilitates intracellular uptake of QDs multifunctionalized (e.g., surface functionalized) with ZFN-IL1Fok1-fluorescent fusion protein cargos.

Single cells and aggregate clusters are treated similar to the NP treatments described in the nanoparticle section and are plated without selection and monitored for the GFP expression colonies two to four weeks after the experiments.

Example 5: Homology-Directed Repair Following SSN Delivery into Tobacco Cells Via GNPs and QDs Target cell lines with integrated ZFN or I-SceI binding sites treated with the ZFN-IL1Fok1 or I-SceI tethered to the particles, as described above, are plated on medium in Petri dishes. Cells are plated onto non-selection medium after the treatments. Green fluorescent foci are visible after seven days. To confirm that the observed fluorescence results from reconstitution of a functional gfp gene, a pool of fluorescing tissue segments are isolated and manually enriched through several passages of selective sub-culture. Genomic DNA is isolated from these fluorescing tissues and assayed by PCR with probes anchored on either gfp gene fragment. Samples enriched from SSN-treated fluorescing tissues, when amplified, yield the predicted 0.6 kb PCR product indicating that the anticipated recombination has reconstituted a functional gfp gene in these tissues. An additional, 4.1 kb PCR product is also observed in the enriched samples, indicating the presence of the non-recombined reporter sequence in the cell population. This is not unexpected given the method of visual selection of fluorescing tissue used to achieve gfp-positive cell enrichment.

While a number of exemplary aspects and embodiments have been discussed above, those of skill in the art will recognize certain modifications, permutations, additions and sub-combinations thereof. It is, therefore, intended that the following appended claims and claims hereafter introduced are interpreted to include all such modifications, permutations, additions and sub-combinations as are within their true spirit and scope.

What may be claimed is:

1. A method of introducing a sequence specific nuclease (SSN) into a plant cell comprising an intact cell wall, the method comprising:
    coating a nanoparticle with a SSN, wherein the nanoparticle has at least one dimension less than 100 nm;
    placing a cell having a cell wall and the coated nanoparticle in contact with each other; and
    allowing uptake of the nanoparticle and the SSN into the plant cell;
    wherein the nanoparticle is selected from the group consisting of porous nanoparticles, mesoporous nanoparticles, silica nanoparticles, polymer nanoparticles, tungsten nanoparticles, gelatin nanoparticles, nanoshells, nanocores, nanospheres, nanorods, magnetic nanoparticles, semiconductor nanoparticles, nanomatrices, dendrimeric nanomatrices and combinations thereof.

2. The method according to claim 1, wherein coating the nanoparticle with the SSN comprises immobilizing the SSN via noncovalent absorption on the surface of the nanoparticle.

3. The method according to claim 1, wherein coating the nanoparticle with the SSN comprises absorption of the SSN into the nanoparticle.

4. The method according to claim 1, further comprising coating the nanoparticle with a subcellular compartment targeting protein.

5. The method according to claim 1, further comprising coating the nanoparticle with a cell penetrating peptide.

6. The method according to claim 4, wherein the nanoparticle is transported into a subcellular compartment of the plant cell.

7. The method according to claim 1, wherein the plant cell comprising a cell wall is selected from the group consisting of tobacco, carrot, maize, canola, rapeseed, cotton, palm, peanut, soybean, *Oryza* sp., *Arabidopsis* sp., *Ricinus* sp., and sugarcane cells.

8. The method according to claim 1, wherein the plant cell is from a tissue selected from the group consisting of embryo, meristematic, callus, pollen, leaves, anthers, roots, root tips, flowers, seeds, pods and stems.

9. The method according to claim 1, wherein the nanoparticle is selected from the group consisting of gold nanoparticles, gold coated nanoparticles, and quantum dots.

10. The method according to claim 1, further comprising derivatizing the surface of the nanoparticle.

11. The method according to claim 1, wherein the SSN is a zinc finger nuclease (ZFN).

12. The method according to claim 11, wherein the ZFN comprises a sequence independent nuclease domain that is derived from the Type IIS restriction endonuclease FokI.

13. The method according to claim 1, further comprising selecting cells that have stably integrated the SSN.

14. The method according to claim 13, wherein the selected cells are regenerable cells.

15. The method according to claim 14, further comprising regenerating a plant from the regenerable cells.

16. The method according to claim 1, wherein the nanoparticle is a multifunctionalized nanoparticle.

17. The method according to claim 6, wherein the compartment is selected from the group consisting of cytosol, nucleus, tonoplasts, plastid, etioplast, chromoplast, leucoplast, elaioplast, proteinoplast, amyloplast, chloroplast, and the lumen of the double membrane.

18. The method according to claim 17, wherein the subcellular compartment is a plastid.

19. The method according to claim 18, wherein the plastid is a chloroplast.

* * * * *